United States Patent
Koldyshev

(10) Patent No.: US 10,311,563 B2
(45) Date of Patent: Jun. 4, 2019

(54) GLASS COATING RECOGNITION SYSTEM AND/OR METHOD

(71) Applicant: Guardian Steklo Services LLC, Ryazan (RU)

(72) Inventor: Maxim Koldyshev, Ryazan (RU)

(73) Assignee: Guardian Steklo Services, LLC, Ryazan (RU)

( * ) Notice: Subject to any disclaimer, the term of this patent is extended or adjusted under 35 U.S.C. 154(b) by 157 days.

(21) Appl. No.: 15/627,573

(22) Filed: Jun. 20, 2017

(65) Prior Publication Data

US 2018/0089821 A1  Mar. 29, 2018

(30) Foreign Application Priority Data

Sep. 23, 2016 (RU) ................... 2016138012

(51) Int. Cl.
*G06K 9/00* (2006.01)
*G06T 7/00* (2017.01)
(Continued)

(52) U.S. Cl.
CPC ............ *G06T 7/0004* (2013.01); *G01N 21/55* (2013.01); *G06F 3/048* (2013.01); *G06F 3/14* (2013.01);
(Continued)

(58) Field of Classification Search
CPC ......... G06T 7/0004; G06T 7/70; G01N 21/55; G01N 2021/8427; H04N 5/2256;
(Continued)

(56) References Cited

U.S. PATENT DOCUMENTS 5,991,018 A   11/1999  Imaizumi et al.
6,576,349 B2   6/2003  Lingle et al.
(Continued)

OTHER PUBLICATIONS

ElektroPhysik: Advancing with Technology Coating "Thickness Measurement with Wireless Sensor and App", Sep. 1, 2015, pp. 1-2.

*Primary Examiner* — Sheela C Chawan

(57) ABSTRACT

Certain example embodiments relate to detecting and recognizing coatings on articles. A captured image and/or video of an article includes source light reflections associated with each major surface of that article. A color coordinate characterization for each source light reflection is calculated. Detection and recognition of any coatings formed on the major surfaces of the article is performable by comparing the calculated color coordinate characterizations and/or changes between calculated color coordinate characterizations to information stored in a data store including known color coordinate characterizations and/or known changes between color coordinate characterizations for different known coatings. Responsive to the detection and recognition of coating(s), there is generated output indicating the major surface(s) on which each detected and recognized coating is formed, an identifier of each detected and recognized coating, a likelihood associated with the detection and recognition of each detected and recognized coating, and an indication of any likely uncoated surfaces.

25 Claims, 12 Drawing Sheets
(9 of 12 Drawing Sheet(s) Filed in Color)

(51) Int. Cl.
  *G06T 7/70* (2017.01)
  *G06F 3/048* (2013.01)
  *G06F 3/14* (2006.01)
  *H04B 10/116* (2013.01)
  *H04B 10/50* (2013.01)
  *H04M 1/02* (2006.01)
  *H04N 5/225* (2006.01)
  *G01N 21/55* (2014.01)
  *G06K 9/46* (2006.01)
  *G01N 21/84* (2006.01)

(52) U.S. Cl.
  CPC .............. *G06K 9/4652* (2013.01); *G06T 7/70* (2017.01); *H04B 10/116* (2013.01); *H04B 10/502* (2013.01); *H04M 1/0202* (2013.01); *H04N 5/2256* (2013.01); *G01N 2021/8427* (2013.01)

(58) Field of Classification Search
  CPC ......... G06F 3/048; G06F 3/14; G06K 9/4652; H04B 10/116; H04B 10/502; H04M 1/0202
  USPC ....... 382/100, 141, 142, 143, 148, 149, 162, 382/181, 274, 305; 702/1, 33, 34, 35, 38, 702/127, 187; 427/331, 384; 324/200, 324/260; 73/866.3, 865.6; 356/625, 630, 356/631, 239.1, 237.1, 239.4, 239.7; 428/411.1, 426, 432, 433; 345/156, 173, 345/174; 204/1, 192.1, 192.12, 192.15; 369/99, 127, 173
  See application file for complete search history.

(56) References Cited

U.S. PATENT DOCUMENTS

| | | | |
|---|---|---|---|
| 7,362,450 B2* | 4/2008 | Zaman | G01N 21/952 356/237.2 |
| 8,204,294 B2* | 6/2012 | Alloo | G01N 25/72 382/141 |
| 8,440,037 B2 | 5/2013 | Dietrich et al. | |
| 8,836,922 B1* | 9/2014 | Pennecot | G01S 17/89 356/4.01 |
| 9,134,466 B2 | 9/2015 | Kreling et al. | |
| 9,403,345 B2 | 8/2016 | Lao et al. | |
| 9,410,359 B2 | 8/2016 | Ding et al. | |
| 2005/0179910 A1* | 8/2005 | Bartov | G01N 21/9501 356/503 |
| 2005/0181219 A1* | 8/2005 | Depauw | C03C 17/38 428/426 |
| 2007/0258093 A1 | 11/2007 | Sieck et al. | |
| 2008/0024798 A1* | 1/2008 | Bartov | G01N 21/9501 356/630 |
| 2011/0313683 A1* | 12/2011 | Chen | G01M 11/088 702/34 |
| 2015/0347854 A1 | 12/2015 | Bare et al. | |

\* cited by examiner

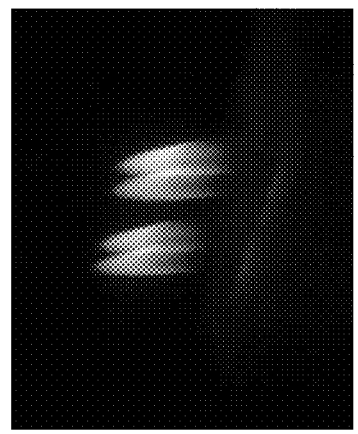
Fig. 8A
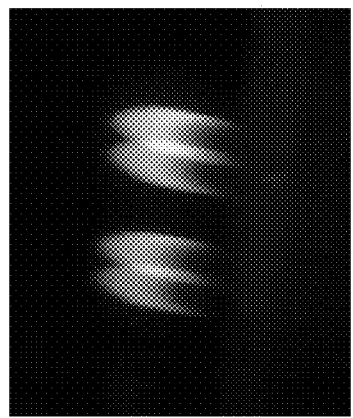
Fig. 8B
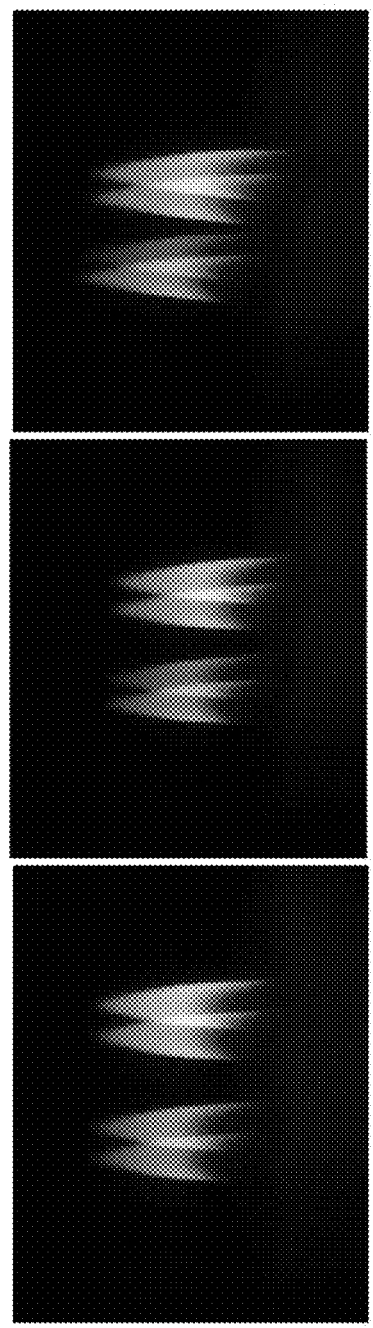
Fig. 9A
Fig. 9B
Fig. 9C

GLASS COATING RECOGNITION SYSTEM AND/OR METHOD

CROSS-REFERENCE TO RELATED APPLICATION

This application is based on and claims priority under 35 U.S.C. § 119 to Russian Patent Application No. 2016138012, filed on Sep. 23, 2016, in the Russian patent office, the disclosure of which is incorporated by reference herein in its entirety.

FIELD OF THE INVENTION

Certain example embodiments of this invention relate to a glass coating recognition system and/or method. More particularly, certain example embodiments of this invention relate to techniques for identifying whether there are any thin film coatings formed on any major surfaces of a coated article or coated article inclusive arrangement (such as, for example, an insulating glass unit) and, if so, what those coatings likely are.

BACKGROUND AND SUMMARY

Coated articles include transparent substrates (e.g., glass substrates) that support coatings on one or more major surfaces thereof. The coatings used in such articles may be functional coatings provided for any number of different reasons. For example, low-emissivity (low-E), solar control, low maintenance, antimicrobial, antireflection (AR), antiglare, and other types of coatings are becoming more and more prevalent in a variety of residential, commercial, vehicle, electronic, and other applications. These coatings may be formed using a variety of different techniques such as, for example, magnetron sputtering, chemical vapor deposition (CVD), combustion deposition, a wet coating technique (such as spin, dip, or other coating technique), etc.

There is a growing demand from end consumers for coated articles. For instance, low-E, solar control, low maintenance, and other types of sputter-deposited or other coatings, can be highly efficient, help buildings conform to energy and/or other standards, etc.

Unfortunately, however, it oftentimes is difficult for end consumers to know, with a suitable level of certainty, that there is in fact a "special" coating applied to one or more surfaces of a coated article. For example, a homeowner might not be able to verify that a low-E coating is formed on a purchased and installed window, that an antimicrobial coating is formed on a shower door, etc. In the majority of cases, the glass coating is so thin (e.g., having a thickness of less than a micron and often times less than a few hundred nanometers) and highly transparent that it is very difficult for end consumers to detect. Even industry specialists can have a difficult time detecting whether there is a coating present without the use of an additional tool (such as a "coating detector" or "spectrophotometers"). Such tools are quite expensive and would not be used by end consumers. Moreover, although some industry specialists may have them, installation crews typically will not have them either.

Thus, it will be appreciated that it would be desirable to have a reliable coating detection and recognition technique that does not necessarily require significant investments into equipment and is available to a broad spectrum of users (including end consumers), worldwide.

Certain example embodiments relate to an electronic coating detection and recognition system comprising a camera. Processing resources include at least one processor and a memory coupled thereto, with the memory tangibly storing instructions that, when performed by the processing resources, at least: capture, using the camera, an image and/or video of an article onto which a source light is shown, the captured image and/or video including source light reflections associated with each major surface of the article; identify a region for each of the source light reflections; calculate a color coordinate characterization for each of the identified source light reflections; detect and recognize any coatings formed on the major surfaces of the article by comparing (a) the calculated color coordinate characterizations and/or changes between calculated color coordinate characterizations to (b) information stored in a database that is backed by a computer readable storage medium and that includes records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed and an identifier of each said detected and recognized coating.

Certain example embodiments relate to an electronic coating detection and recognition system comprising a camera. Processing resources include at least one processor and a memory coupled thereto, with the memory tangibly storing instructions that, when performed by the processing resources, at least: capture, using the camera, an image and/or video of an article onto which a source light is shown, the captured image and/or video including source light reflections associated with each major surface of the article; and transmit, over a network connection, the captured image and/or video to a remote computer system. The transmission causes the remote computer system to: receive the captured image and/or video; calculate a color coordinate characterization for each of the source light reflections in the received captured image and/or video; detect and recognize any coatings formed on the major surfaces of the article by comparing (a) the calculated color coordinate characterizations and/or changes between calculated color coordinate characterizations to (b) information stored in a data store of the remote computer system that includes records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed and an identifier of each said detected and recognized coating.

Certain example embodiments relate to an electronic coating detection and recognition system comprising a camera. Processing resources include at least one processor and a memory coupled thereto, with the memory tangibly storing instructions that, when performed by the processing resources, at least: receive a captured image and/or video of an article onto which a source light is shown, the captured image and/or video including source light reflections associated with each major surface of the article; calculate a color coordinate characterization for each of the source light reflections in the received captured image and/or video; enable detection and recognition of any coatings formed on the major surfaces of the article by comparing (a) the calculated color coordinate characterizations and/or changes between calculated color coordinate characterizations to (b) information stored in a data store, the data store including records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed, an identifier of each said detected and recognized coating, a likelihood associated with the detection and recognition of each said detected and recognized coating, and an indication of any likely uncoated surfaces.

Methods for using and/or configuring these and/or other systems also are contemplated herein. Similarly, non-transitory computer readable storage media tangibly storing instructions that, when executed by a hardware processor, perform these and/or other methods also are contemplated herein.

The features, aspects, advantages, and example embodiments described herein may be combined to realize yet further embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features and advantages may be better and more completely understood by reference to the following detailed description of exemplary illustrative embodiments in conjunction with the drawings, of which:

FIGS. 8A-8B demonstrate how the angle at which the reflection is imaged affects the image recognition for a coating applied to the second surface of an IG unit, in certain example embodiments;

FIGS. 9A-9C demonstrate how the angle at which the reflection is imaged affects the image recognition for a coating applied to the third surface of an IG unit, in certain example embodiments;

DETAILED DESCRIPTION OF EXAMPLE EMBODIMENTS OF THE INVENTION

Figure 1:
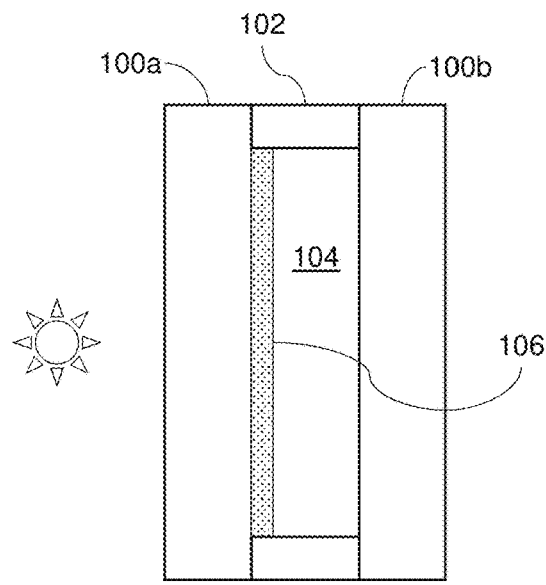
FIG. 1 is a schematic view of an insulating glass (IG) unit that may be the subject of certain example embodiments.

Certain example embodiments relate to techniques for detecting and recognizing thin coatings (e.g., thin film coatings) formed on the major surfaces of coated articles and coated article inclusive arrangements. In certain example embodiments, a light source (which in some instances may be a uniform or substantially uniform light source such as, for example, light from a gas-lighter, candle, LED light, or the like) is shown on the article, and the spectrum of its reflection (from the coated glass and/or other surfaces) is captured using a digital camera or other imaging means and analyzed. This approach advantageously makes it possible to detect the presence of the coating on the surface, and also makes it possible to recognize the type of the coating with high accuracy. To improve accuracy, certain example embodiments may incorporate training techniques, e.g., such that different types of coatings may be recognized, different types of articles may be considered, different types of light sources may be used, etc.

In certain example embodiments, a commercially available smartphone, tablet, or other electronic device, may have installed thereon an application (or app). The application in certain example embodiments uses the electronic device's built-in or otherwise connected camera to image reflections created when a light source is shown on the article. The light source may be the electronic device's built-in or otherwise connected LED light, light from a lighter, and/or the like. Advantageously, end consumers and others may be able to easily detect and recognize the type of coating(s) formed on the surface(s) of the article. In certain example embodiments, a low-cost dedicated device may be used. In certain example embodiments, the dedicated device may be built into and/or otherwise provided with packaging in which the article ships. Including a dedicated device with packaging may be advantageous in certain example instances, as the device may be oriented at the device at an angle suitable for imaging, a known light source may be used at a good angle and distance from the article to be imaged, the packaging may help create desirable ambient lighting conditions (e.g., a very dark background), etc. In addition, incorporating the light and/or electronic device in packaging may help reduce the likelihood of the device, light source, and/or article to be imaged from falling and/or becoming damaged during the coating detection and recognition operations.

Because many magnetron sputtering coatings are deposited on the "air side" of a float glass surface (e.g., using a so-called "offline method") and perform on the basis of certain wavelengths reflection (e.g., in the case of low-E coatings, for example) of the initial visible light/infrared radiation, it was experimentally confirmed that reflected light (as well as transmitted light) changes its initial wavelength. This change corresponds to the type of coating applied on the glass surface. The change of the reflected wavelength oftentimes is difficult to detect by the human eye. In fact, one goal of coating design oftentimes is to minimize transmitted and/or reflected color change, especially within visible ranges. This goal therefore intrinsically makes detecting changes in reflected wavelength more difficult. However, computer-assisted visioning (e.g., using modern cameras installed into smartphones or used separately for the offline image analysis) can facilitate this detection and enable subsequent recognition.

Referring now more particularly to the drawings in which like numerals indicate like parts throughout the several views, this principle is demonstrated in connection with FIGS. 1-5. FIG. 1 is a schematic view of an insulating glass (IG) unit that may be the subject of certain example embodiments, and FIGS. 2-4 help demonstrate how light source reflection colors differ based on the presence/absence of a coating on a substrate and thus may be detected and recognized in accordance with certain example embodiments.

The IG unit of FIG. 1 includes first and second substantially parallel spaced apart substrates 100a and 100b. The first and second substrates 100a and 100b may be glass, plastic, and/or the like. The first and second substrates 100a and 100b are maintained in substantially parallel spaced apart relation to one another via a spacer system 102. The first and second substrates 100a and 100b, together with the spacer system 102, define a gap or cavity 104 therebetween. The gap or cavity 104 may be filled with at least partially filled with an inert gas such as, for example, Ar, He, Kr, Xe, and/or the like. In some instances, the gap or cavity 104 may be filled with a mixture of air and an inert gas. One or more thin film or other coatings may be formed on one or more major surfaces of the first substrate 100a and/or the second substrate 100b. For instance, as shown in FIG. 1, a thin film coating 106 is formed on an inner surface of the first substrate 100a (i.e., surface 2 of the IG unit of FIG. 1, facing the second substrate 100b).

Figure 2:
FIGS. 2-4 help demonstrate how light source reflection colors differ based on the presence/absence of a coating on a substrate and thus may be detected and recognized in accordance with certain example embodiments.
Figure 3:
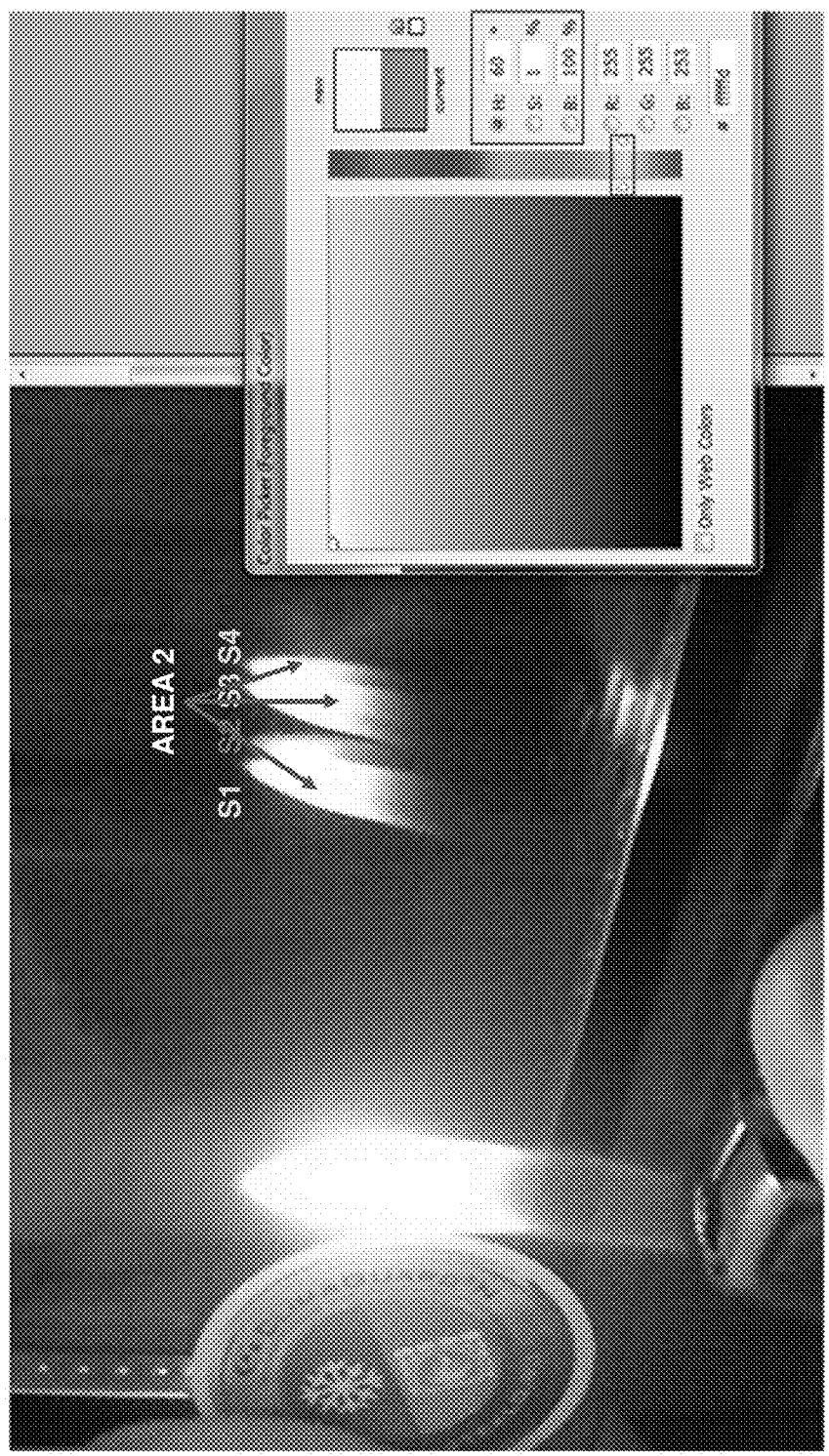
Figure 4:

FIGS. 2-4 involve an IG unit having the ClimaGuard N coating applied to its second surface. ClimaGuard N is commercially available from the assignee. The flame from a commercially available lighter is ignited just outside of surface 1 of the IG unit. Because the flame and IG unit in FIGS. 2-4 are in a relatively dark environment, four reflections of the flame are cast, with one reflection corresponding to each major surface of the IG unit. These surfaces are identified as #1, #2, #3, and #4. With respect to FIG. 2, the spectrum of the flame itself (in "Area 1") can be analyzed and classified according to a known coordinate system such as, for example, the HSB, the RGB, CMYK, or other coordinate system, or classified using a hexadecimal or other representation. In the FIG. 2 example, the flame has a core that is basically white, and the HSB color coordinate representation is defined as H=0, S=0, B=100.

Referring to FIG. 3, it can be seen that each of the uncoated surfaces ("Area 2") have a reflection of the flame with the same or very similar generally yellow color. Here, the reflected flame on the uncoated surfaces has an HSB color coordinate representation defined as H=60, S=1, B=100. By contrast, it can be seen from FIG. 4 that the coated surface ("Area 3") has a reflection of the flame with a very different coloration. That is, the HSB color coordinate representation for Area 2 is defined as H=300, S=1, B=100.

The flame in this case is the original light source, which itself may be used for calibration purposes. The uncoated surfaces have the same or very similar color in the respective core flame reflection. By contrast, the coated surface has a color that is different from the core flame reflections, and the core flame itself.

Although different coatings may have their own distinct reflection range spectra, by having a database of images made via various cameras and in different lightning conditions, it is possible to educate the system to recognize such coatings from one or more images, and/or by analyzing a video that captures reflections via smartphone, tablet, or other electronic device. Further detail on these example techniques is provided below. In addition, it will be appreciated that some coatings may be very close in reflection coloration. Therefore, the probability of successful recognition may be calculated and displayed to the user of the application.

Figure 5:
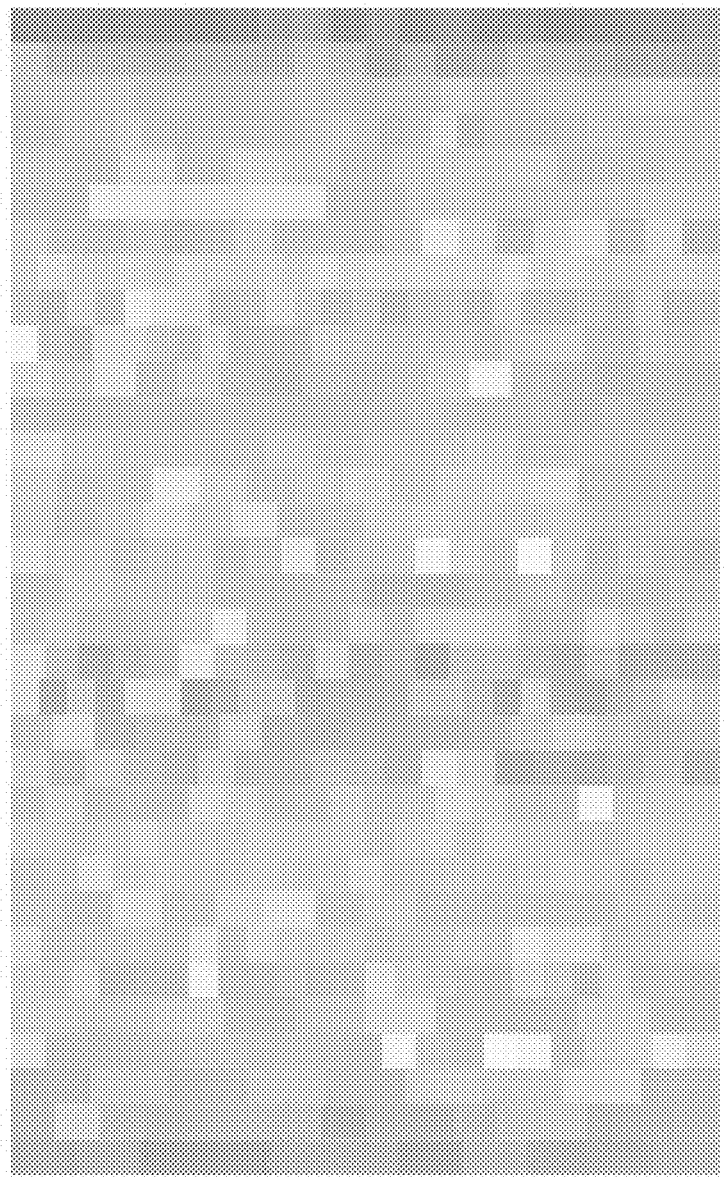
FIG. 5 is a matrix showing the coloration of different types of coatings, as derived in and usable with certain example embodiments.

FIG. 5 is a matrix showing the coloration of different types of coatings, as derived in and usable with certain example embodiments. FIG. 5 shows colors for 20 different samplings of different coatings commercially available from the assignee. Information indicative of this coloration may be stored in a database for consultation. For example, the information may include a range of HSB or other coordinates, a mean value of the HSB or other coordinates, a median value of the HSB or other coordinates, and/or the like. This information may be associated with an identifier of the coating, a surface on which the coating typically is applied, etc. Example records are set forth below:

| Coating Name | Color coordinates (L, a*, b*); (RGB) |
|---|---|
| ClimaGuard N, Surface #3 | (26.16, 2, −7); (59.73, 61.42, 71.87) |
| ClimaGuard Solar, Surface #2 | (54.03, 1, −6.5); (125.48, 129.14, 139.18) |
| ClimaGuard Titan, Surface #2 | (30.7, −2, −8); (61.8, 73.79, 83.87) |
| ClimaGuard Titan, Surface #3 | (58.6, 0.2, −2); (139.65, 141.04, 143.26) |

Figure 6:
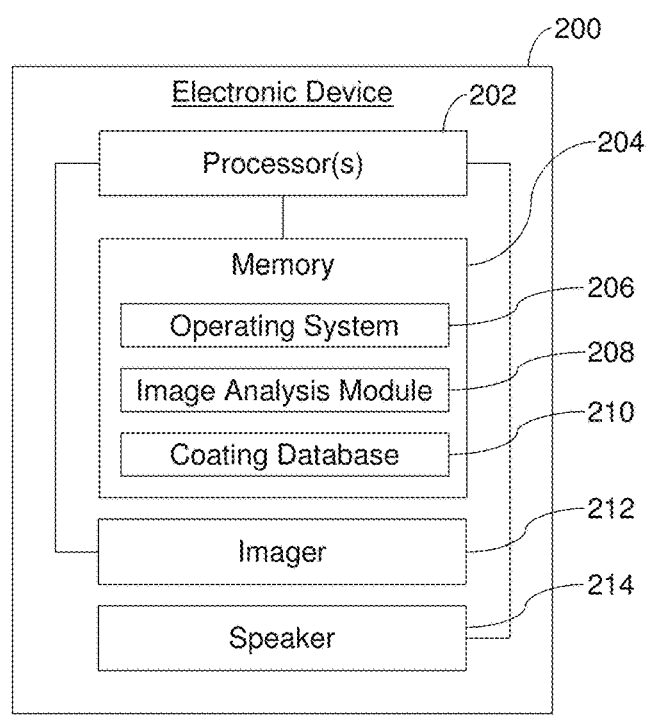
FIG. 6 is a block diagram of an electronic device that includes an image analysis module for coating detection and recognition in accordance with certain example embodiments.

These techniques may be embodied in a computer system such as, for example, an electronic device, a computer system including an electronic device, and/or the like. For example, FIG. 6 is a block diagram of an electronic device 200 that includes an image analysis module 208 for coating detection and recognition in accordance with certain example embodiments. The electronic device 200 of FIG. 6 includes processing resources comprising at least one processor 202 operably coupled to a memory 204. The memory 204 may be any suitable combination of transitory and/or non-transitory memory such as, for example, RAM, ROM, flash memory, hard disk drive memory, and/or the like. The memory 204 may include stored instructions that, when executed by the processor(s) 202, cause the electronic device 200 to perform computerized functionality. In this regard, the memory 204 includes an operating system 206 suitable for electronic device 200. If the device 200 is a smartphone, tablet, or the like, the operating system 206 may be an Android, iOS, or other operating system, which may be embedded in the device 200. If the device 200 is personal computer, laptop, or the like, the operating system 206 may be a Windows, MAC, or other operating system. In some cases, the operating system 206 may be a custom, lightweight embedded operating system.

The operating system 206 is able to support the running of an image analysis module 208 and provide or otherwise mediate access to the coating database 210. The coating database 210 may include information of the type described above, and it may be stored local to the device 200 (e.g., in the memory 204), or external to device 200 (e.g., hosted on an external server or other computer system, as explained in greater detail below).

The image analysis module 208 may be configured to control the device 200 to use the imager 212 to take still pictures, video, and/or the like. Similarly, the image analysis module 208 may be configured to perform white-balancing operations, actuate a flash using a light source of or otherwise accessible to the electronic device 200, etc. The image analysis module 208 also may be configured to interface with, or obtain information from, an accelerometer, gyroscope, or other device of or connected to the device 200. This information may be useful in calculating a tilt or attitude of the device, e.g., relative to the surface of an article to be imaged using the imager 212. In certain example embodiments, the imager 212 is simply a camera built into a smartphone, tablet, or the like. The image analysis module 208 may perform coating detection and/or recognition functions of the type described in greater detail below, e.g., with respect to captured still images and/or video, and/or it may communicate with an external system so that image processing may be performed remote from the device 200.

Once the image and/or video has been processed, the image analysis module 208 may present resultant information to the user via a display device of or connected to the electronic device 200. Example user interface screens are described in greater detail below. Additionally, or in the alternative, in certain example embodiments, the resultant information may be emailed to a user, sent via SMS or MIMS to a phone or other device of a user (e.g., if that information has been pre-provided), provided in a written report that later is mailed to a user, etc.

In certain example embodiments, the electronic device 200 includes a built in speaker 214. The speaker may be used to provide audio feedback, e.g., when the electronic device is put into proper orientation relative to the article to be imaged, when the image and/or video is captured, when processing begins and/or completes, etc.

As alluded to above, the electronic device 200 may be embedded in or otherwise connected to packaging of or associated with the article to be imaged.

Figure 7:
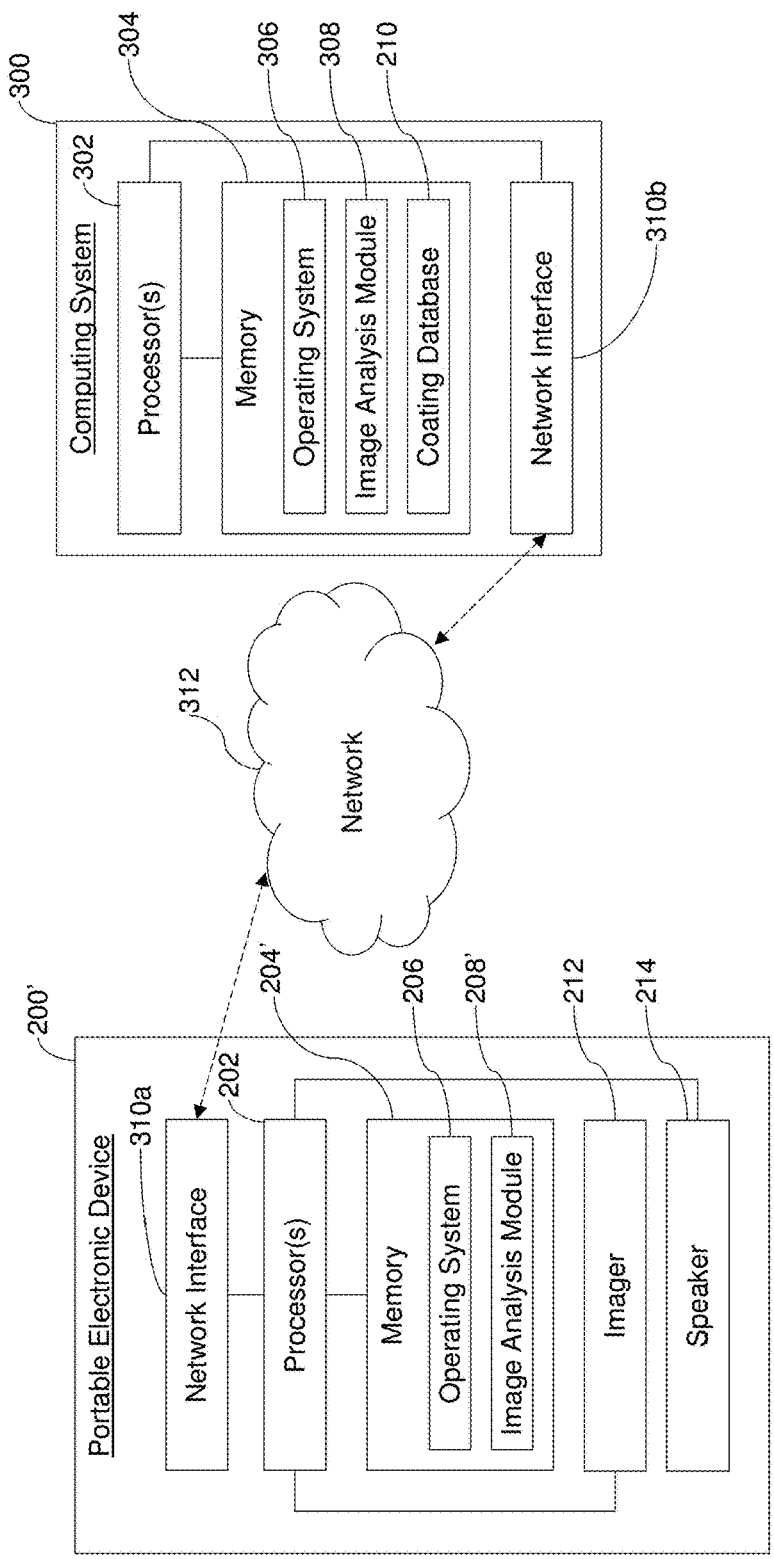
FIG. 7 is a block diagram of a system that includes image analysis modules that cooperate for coating detection and recognition in accordance with certain example embodiments.

FIG. 7 is a block diagram of a system that includes image analysis modules 204' and 308 that cooperate for coating detection and recognition in accordance with certain example embodiments. FIG. 7 is similar to FIG. 6, except that at least some of the coating detection and recognition is performed at a remote site. In this regard, a portable or other electronic device 200' includes processing resources comprising one or more processors 202 and a memory 204' operably coupled thereto. The memory includes an operating system 206, and a potentially lighter-weight image analysis module 208'. In certain example embodiments, the potentially lighter-weight image analysis module 208' interfaces with the imager 212 to obtain still images and/or videos, and coordinates with the network interface 310a to send that information to a remote site for processing. As shown in the FIG. 7 example, the network interface 310 of the portable or other electronic device 200' transmits information to a remote computing system 300 over a network 312. The network may be a local area network (LAN), wide area network (WAN), wireless network (e.g., a 3G, 4G/LTE, or other network), and/or the like. In certain example embodiments, the network interface 310a may include interfaces for communication with the network 312 by an 802.11 wireless or other standard, a cellular standard, Bluetooth, or other suitable protocol. In certain example embodiments, the portable or other electronic device 200' communicates with the remote computing system 300 directly, e.g., on a peer-to-peer basis, potentially bypassing the network 312.

The computing system 300 also includes processing resources. These processing resources similarly comprise at least one processor 302 and a memory 304 operably coupled thereto. The memory 304 stores an operating system 306, a separate image analysis module 308, and the coating database 210. Information may be received at the computing system 300 via its network interface 310b.

The information that may be received at the computing system 300 includes still and/or video images captured using the imager 212 of the portable or other electronic device 200', as relayed to it via the image analysis module 208' of the portable or other electronic device 200'. Here, the computing system 300 may be more powerful than the portable or other electronic device 200' and thus may process the still and/or video images captured using the imager 212 of the portable or other electronic device 200', compare the data to information stored in the coating database 210, and determine whether there likely are any coatings on the article that has been imaged and, if so, where they are and what they likely are. Once processing has been performed at the computing system 300, that information may be relayed back to the portable or other electronic device 200' via the network interface 310b. Once received, the image analysis module 208' may present resultant information to the user via a display device of or connected to the portable or other electronic device 200'. As noted above, additionally, or in the alternative, in certain example embodiments, the resultant information may be emailed to a user, sent via SMS or MIMS to a phone or other device of a user (e.g., if that information has been pre-provided), provided in a written report that later is mailed to a user, etc.

It has been found that reflection color depends on the angle of imaging. That is, the reflection differs when the light source is normal to the surface of the article, and when it is "off-axis" compared to normal. The type and extent of the difference has been found to depend on the coating. For example, some coatings involve only saturation changes, while others may have changes in both saturation and color tone. Having knowledge of the changes that occur at different angles of illumination can aid in detection and recognition accuracy. FIGS. 8A-8B demonstrate how the angle at which the reflection is imaged affects the image recognition for a coating applied to the second surface of an IG unit, in certain example embodiments, and FIGS. 9A-9C demonstrate how the angle at which the reflection is imaged affects the image recognition for a coating applied to the third surface of an IG unit, in certain example embodiments.

More particularly, FIGS. 8A-8B involve the Neutral 80/58 (ClimaGuard Premium T+) coating available from the assignee on the second surface of an IG unit. In FIGS. 8A-8B, the light sources are candle flames, which are angled 40 and 60 degrees from the surface of the article, respectively. FIGS. 9A-9C also involve the Neutral 80/58 (ClimaGuard Premium T+) coating available from the assignee, but here, the coating is are provided on the third surface of the IG unit. In FIGS. 9A-9C, the light sources are candle flames, which are angled 40, 50, and 60 degrees from the surface of the article, respectively. It can be seen that there is good separation of the reflected flames, and that the color change for the coated surface is distinct. Certain example embodiments thus may involve imaging at angles of 30-75 degrees from the surface of the article to be imaged, more preferably 40-60 degrees and, for example, 45 degrees. The 45 degree angle has been found to work especially well with a variety of coatings, e.g., in providing good separation of the reflected flames (thereby facilitating easy and accurate detection of the reflections) and good color changes for coated surfaces (thereby facilitating easy and accurate recognition of the reflections). In certain example embodiments, a database may be built based on a common angle, and this "trained angle" or an angle close to it (e.g., within about 5-10 degrees) may be used in certain example embodiments.

Figure 10:
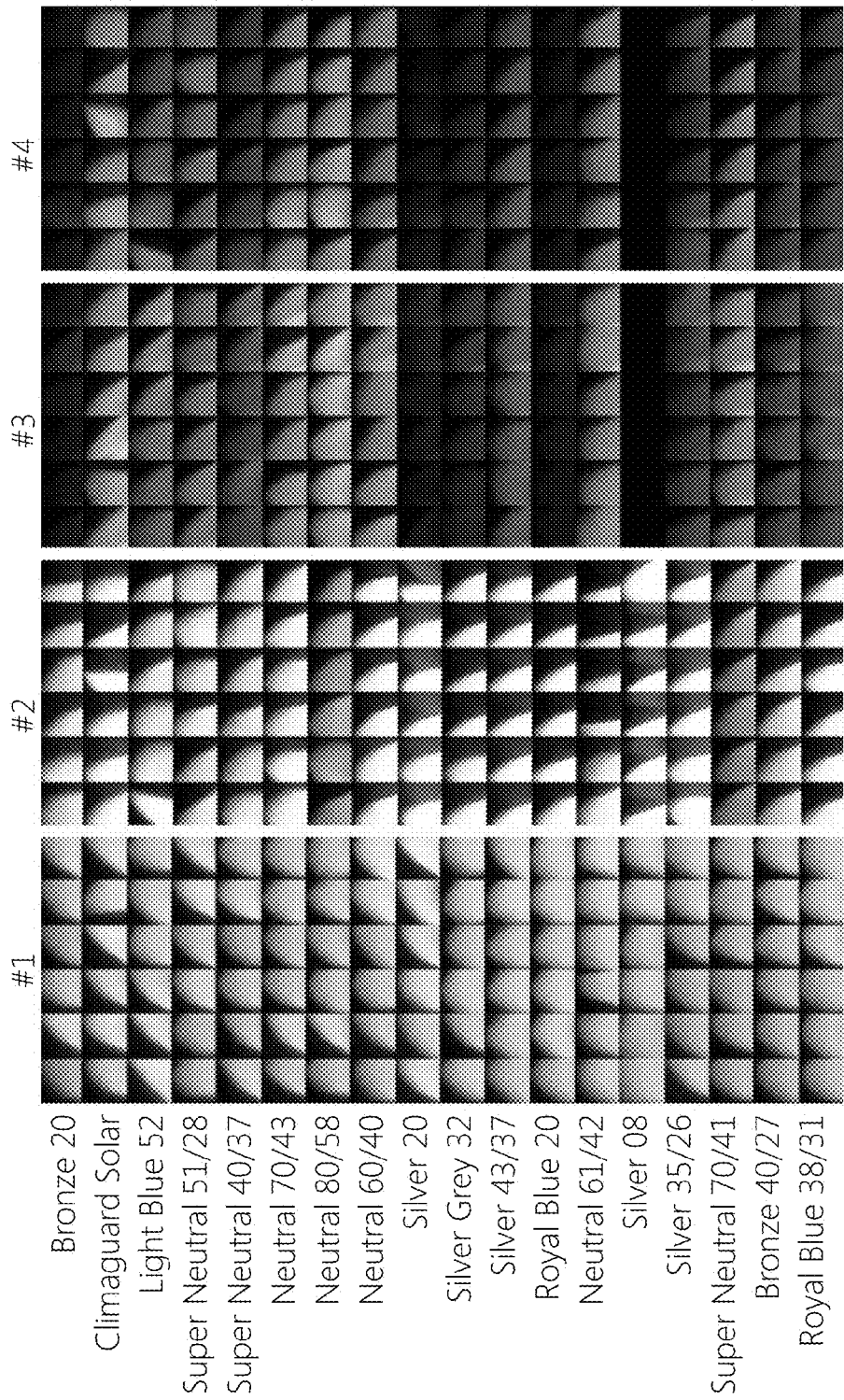
FIG. 10 is a matrix showing light source reflections for different types of coatings applied to the second surface of an IG unit, derived and usable in connection with certain example embodiments.

FIG. 10 is a matrix showing light source reflections for different types of coatings applied to the second surface of an IG unit, derived and usable in connection with certain example embodiments. The matrix shows different samples of IG units having coatings applied thereto. The samples were taken in laboratory conditions. Using this sampling information, it is possible to train certain example embodiments to work with different white balances. This becomes possible because certain example embodiments may consider the color changes from one reflection to another in place of, or in addition to, the single reflections. In other words, samples may be obtained in certain example embodiments and, in place of or in addition to storing information about the coloration of the reflections for each of plural different arrangements, the coloration changes may be tracked from surface-to-surface for each of plural different arrangements. It will be appreciated that the training may be accomplished using images taken from the surface 1 side of the IG unit, and/or the surface 4 side of the IG unit. That is, certain example embodiments may be trained from the outside, and/or from the inside, major surface(s) of the articles to be imaged. In certain example embodiments, a user may be prompted to take images from both the inside and the outside of the article to be imaged, e.g., to help improve accuracy through the gaining of more raw information.

Figure 11:
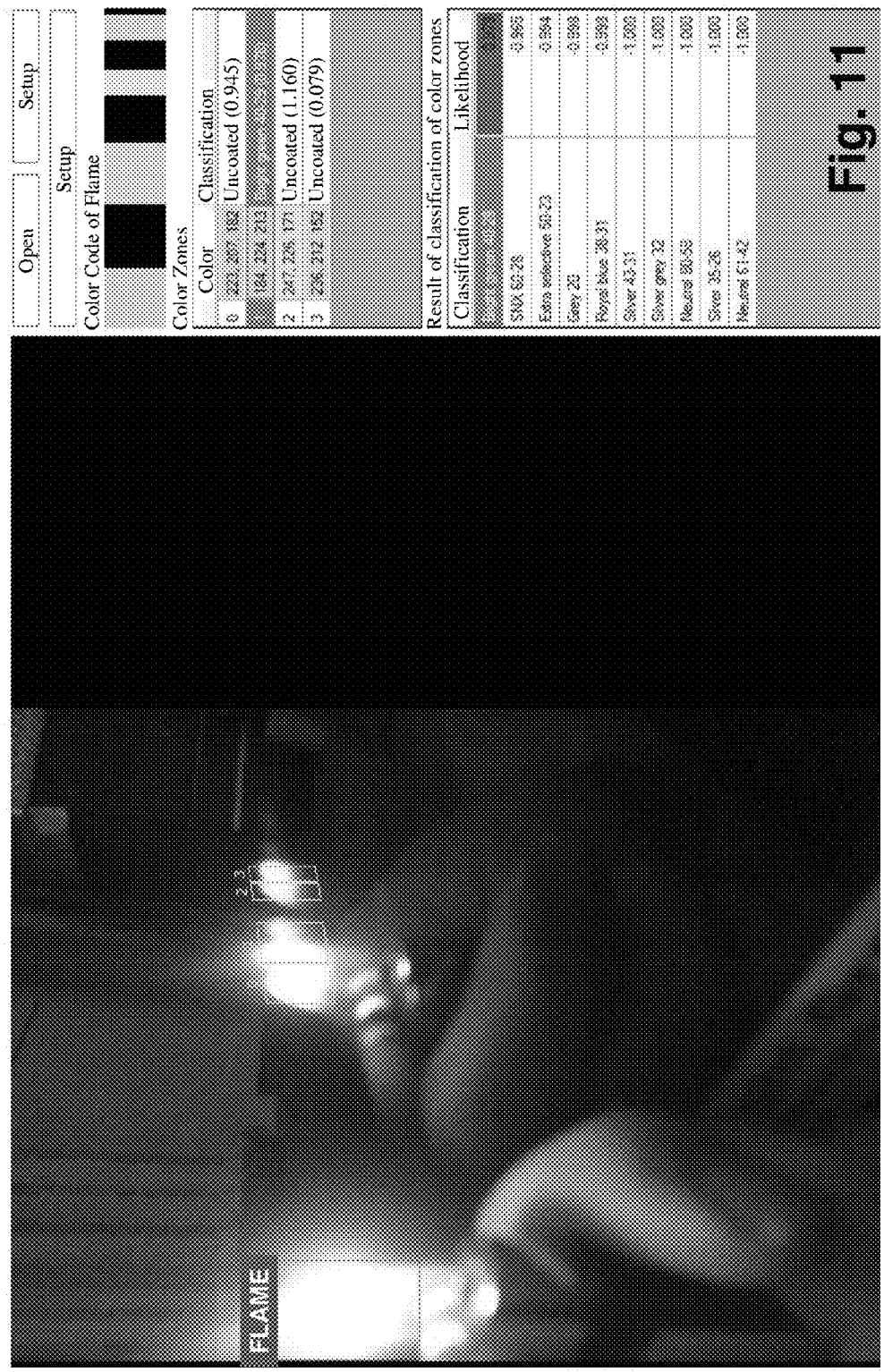
FIGS. 11-13 are screenshots of an application detecting and recognizing different coatings on surfaces of different insulating glass (IG) units, in accordance with certain example embodiments.
Figure 12:
Figure 13:

FIGS. 11-13 are screenshots of an application detecting and recognizing different coatings on surfaces of different insulating glass (IG) units, in accordance with certain example embodiments. Each of FIGS. 11-13 includes, at its left, a still image capture of an IG unit, a flame, and reflections of the flame. As a result of the image processing, the still image may be annotated to indicate the flame's position, as well as the positions of each of the reflections and the surfaces with which they are associated. In these examples, the numbers of the reflections correspond to the surface number of the IG unit, minus 1. On the right side of each of the images, the main, dominant, average, or median color coordinates for each of the reflections is shown in a given color coordinate system, along with an indication indicative of the surface associated with the reflection. In this example, the HSB color coordinate system is used. Next to this color information is an indication as to whether the associated surface is coated and, if so, what coating likely is on that surface. A probability value for the recognition also is provided in certain example embodiments.

When a user selects a given surface, the result of the classification is shown. As shown in FIGS. 11-13, this includes a list of coatings, in descending order of likelihood of that coating being the coating on the surface (if any). FIG. 11 shows the Bright Green 40-29 coating of the assignee's being on surface 2, FIG. 12 shows the Neutral 60-40 coating of the assignee's being on surface 2, and FIG. 13 shows the Super Neutral 70-37 coating of the assignee's being on surface 2. If the coating detection is less than a given threshold (e.g., 90% or 95%), certain example embodiments may further include a visual indicator so that the recognition can be gauged in a more visual way. As an example, FIGS. 12-13 include horizontal bars as example indicia.

Figure 14:
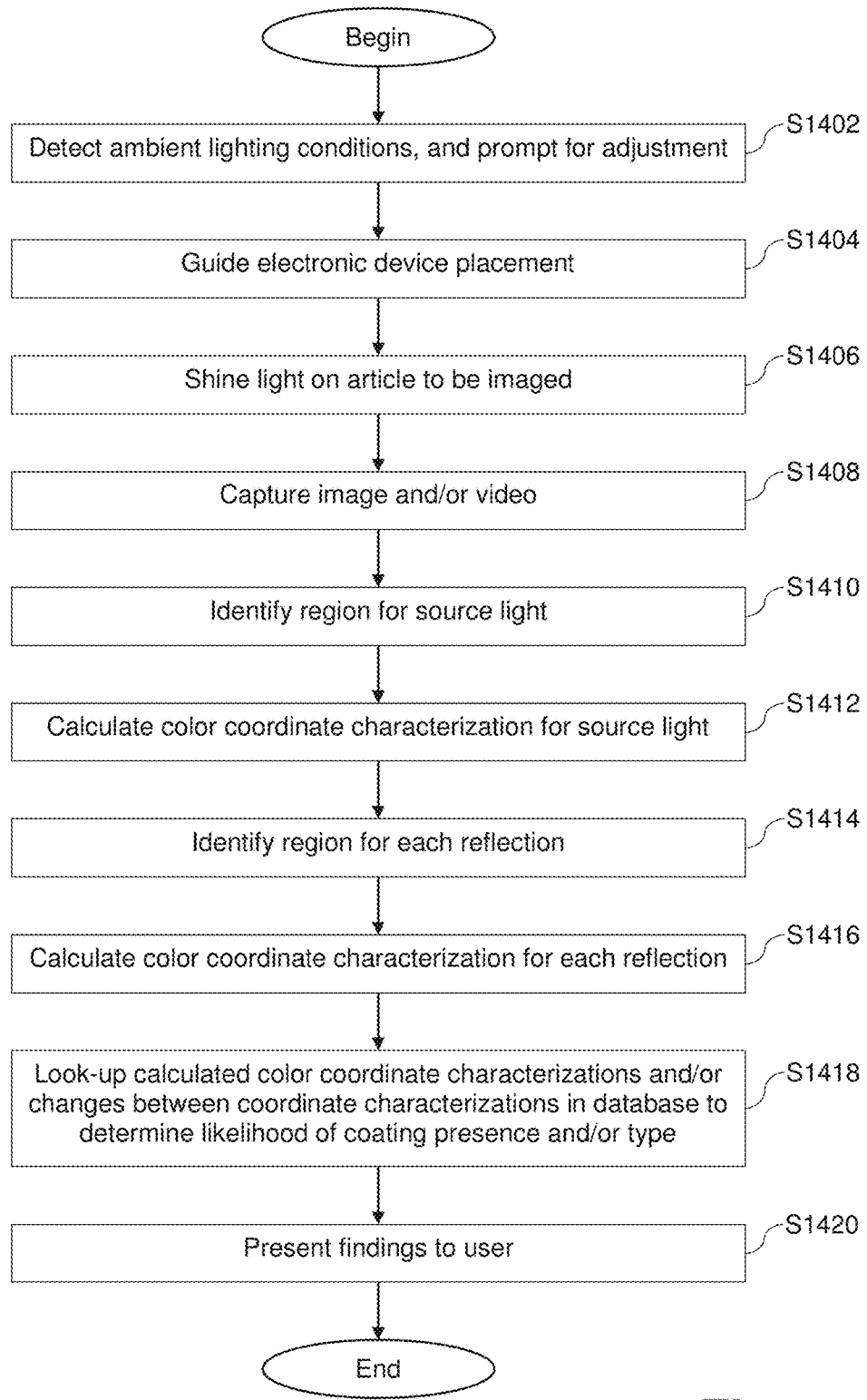
FIG. 14 is a flowchart showing how the coating recognition system of certain example embodiments operates.

FIG. 14 is a flowchart showing how the coating recognition system of certain example embodiments operates. In step S1402, ambient lighting conditions are detected, e.g., using a camera, IR detector, or other imaging element of an electronic device. If necessary or desirable (e.g., if the ambient light likely is too high to produce reliable reflections), an application running on the device may prompt the user to alter the lighting conditions. For example, an audiovisual, text-based, or other prompt, may suggest that the lights should be dimmed or cut off, that backlighting is too high, etc. An audiovisual, text-based, or other prompt may indicate to a user of the application when the ambient lighting conditions are determined to be good.

In step S1404, the user of the application is guided in the placement of the electronic device. This may include, for example, visually showing or otherwise describing how the device should be oriented relative to the article to be imaged. For example, icons may be used to show that the electronic device should be placed close to the inner or outer surface of the article and at a given angle. Using an accelerometer, gyroscope, IR detector, camera, and/or the like, the attitude or tilt of the electronic device relative to the surface may be detected. Once the position is determined to be accurate (e.g., at or close to a desired angle or angle range), an audio prompt may be provided. The audio prompt may be desirable, as it may be difficult to see a visual indication on a display screen of the device, depending on its placement relative to the article to be imaged.

In step S1406, the light is shined on the article to be imaged. The light may be built into or otherwise connected with the electronic device. For example, a smartphone's LED light or the like may be used in certain example embodiments. In certain example embodiments, a lighter, candle flame, pen light, a light built into packaging such as a carton or box, a white or other colored image (e.g., a square, circle, stylized object that is easy to recognize with computer visioning techniques, and/or the like) provided on a screen of an electronic device (such as a smartphone, tablet, or the like), or other source of light may be used. Preferably, the light is highly directional. Optical elements may be used to help ensure that this is the case.

In step S1408, an image and/or video of the article is captured. The capturing may be performed by a camera of or connected to the electronic device, and it may occur automatically (e.g., within a predetermined time of the user being prompted to place the electronic device in an appropriate position relative to the article to be imaged, once the angle is determined to be correct, etc.), and/or manually (e.g., once a button on the display screen, a side surface, and/or the like is pressed. In certain example embodiments, a shutter button may cause the picture to be taken. In certain example embodiments, pressing a button ordinarily reserved for volume adjustment, power-related functionality, accessing the home screen, or the like, may be overridden so that an image or video is captured. This technique may make it comparatively easier to manually take the image or capture the video while still holding the device in a proper orientation relative to the article to be imaged.

Step S1408 may include adjusting the white balancing of the camera, and/or changing the focus of the device. In certain example embodiments, autofocusing may be used. In other cases, autofocusing may focus on the wrong item (e.g., a reflection or other element that results in poor image quality). Thus, autofocusing may be disabled in certain example embodiments. Instead, certain example embodiments may use a fixed focus, computed based on the device used, the placement of its camera, its angle relative to the article to be imaged, and/or the like. In this regard, certain example embodiments may involve an application loaded on a smartphone or the like, and the type of device may be determined by the application. Using this information, the device may look-up focus settings (e.g., because certain devices may be known to have certain camera placements, the distance can be calculated based on the device's known form factor and the angle determined in accordance with the above, etc.) and/or otherwise calculate such settings. In certain example embodiments, automatic adjustments typically made by some cameras may be overridden by setting an ISO mode, and/or the like.

In certain example embodiments, the light integrated into the device may not by itself be suitable for good imaging. For example, although many smartphones, tablets, and other devices use LED lights, optical elements oftentimes are used to disperse what otherwise might be very linear sources of light. Diffusers are oftentimes used in the flashes of cameras, smartphones, tablets, and/or the like. Thus, a clip-op or other optical element may be used to make more linear or otherwise focus the light into a more directional and more desirable form, e.g., to at least partially undo the effect of a built-in or otherwise integrated diffuser.

Referring once again to FIG. 14, in step S1410, the region of the source light is identified, e.g., from the image and/or video. In an image, the source light likely will be the brightest element at one of the edges of the still picture that is taken (e.g., the brightest element at the left or right of the picture). Any object detection technique may be used for this purpose. For example, once a bright spot is detected at the edge, the rough contours of the object may be determined by proceeding outwardly in both horizontal and both vertical directions, by spiraling outwardly from a detected edge, and/or the like, e.g., until an area of color contrast greater than a threshold is reached. This might, for example, correspond to the transition between the bright source light and the dark ambient conditions. The contours then may be specified by following the edges of the object (e.g., tracing areas where the threshold is tripped), treating the maximal vertical and horizontal areas as being a generally rectangular area, and/or the like. The bounded area may be considered the source light object. In certain example embodiments, an automatic image processing technique such as this may be used to detect the source light object. In certain example embodiments, the source light object may be manually identified (e.g., by a user of the application). In certain example embodiments, a candidate for the source light object may be automatically detected, and manual confirmation may be requested or required.

In step S1412, the color coordinate characterization for the source light object is calculated. This may be accomplished by selecting the value at the center of the object, by selecting the value at the approximate horizontal center of the object and slightly higher than vertical center of the object, by calculating the average or median color coordinates, by having the user manually select a value, and/or the like. In certain example embodiments, a candidate for the color coordinate characterization for the source light object may be automatically detected, and manual confirmation may be requested or required.

Steps S1414 and S1416 perform generally similar functions as those explained above in connection with steps S1410 and 1410, except that steps S1414 and S1416 operate with respect to the regions of the reflections and color coordinate characterizations for the reflections. This process may be facilitated if the user inputs the type of article being imaged. For example, specifying that the article being imaged is a single substrate will instruct the device to look for two distinct reflections, specifying that the article being imaged is an IG unit will instruct the device to look for four distinct reflections, etc. Further specifications of the article being imaged may further aid in accuracy. For example, specifying substrate thickness, spacer thickness and/or gap spacing, etc., may provide information as to where the reflection objects should appear relative to one another, how far apart they should be spaced, etc. In certain example embodiments, based on reflections, glass thickness and gap depth may be detected. Furthermore, once glass thickness is known, angle may be detected more easily in some situations. It is noted that the same or similar auto-recognition and/or manual color picking/verification techniques may be used for training purposes, as well, e.g., to build a suitable database of images.

In certain example embodiments, some or all of steps S1408-1414 may be performed local to the electronic device or on a device remote from it. For example, a standalone digital camera may be used to capture a still image or video, and image processing may be performed "offline" on an external computer system, with the results of the analysis possibly being presented on that or another external computer system. In certain example embodiments, color coordinate characterizations may be provided via manual selections.

Based on the calculated color coordinate characterizations and/or calculations concerning the changes between coordinate characterizations for adjacent or sequential objects, a database lookup may be performed. Doing so may help to determine the likelihood of one or more coatings being present and may also help determine position and type information for any such coating(s). This also includes the detection and recognition of uncoated surfaces. Lookups may be performed by calculating the distance between coordinate characterizations for objects and color coordinates stored in the database for the different coatings. Based on Euclidian or other distance measures, for example, a rank ordering of likely coating types may be determined. Likelihood of a match may be based on the same or other distance measures in certain example embodiments. The same or similar technique may be used when color coordinate changes are used. It will be appreciated that a comparison between a known light source and a first reflection may be used to determine and/or compensate for white balancing, calibration of color temperatures, and/or the like.

In step S1420, findings are presented to the user via the application, a message sent the user via email, SMS, MIMS, or other messaging means, and/or the like. The findings may include, for example, an annotated version of a still image (e.g., if a still image is taken, or as extracted or generated from a video) may include indicia of the flame area and the area of each reflection, and/or a labeling of surfaces for the reflections. Some or all of the information described in connection with FIGS. 11-13 and/or the like also may be provided in certain example embodiments. Based on the outcome, the user can know, with a specified degree of likelihood, whether there are any coated surfaces on a product and, if so, what the coatings on such surfaces likely are. Preferably, certain example embodiments are able to recognize coatings with at least 80% accuracy, more preferably at least 85% accuracy, still more preferably at least 90% accuracy, and still more preferably at least 95% accuracy.

In certain example embodiments, the procedure described above may be repeated in whole or in part to try to confirm the accuracy of the detection and recognition. The repetition may be from the same side, from the opposite side, or from both the same side and the opposite side.

It has been observed that some highly reflective coatings sometimes produce a "phantom" third reflection. Certain example embodiments may take this into account and eliminate it, use its detection as indicator of a particular coating type, and/or the like.

In certain example embodiments, the system may be trained with competitor products to look for them, to make sure that the application is being used on the proper product (e.g., without officially reporting that a competitor's coating has been detected and/or recognized with a high probability of accuracy), etc.

Although certain example embodiments have been described in connection with the HSB color coordinate system, it will be appreciated that other systems and/or representations may be used in different example embodiments. This includes, for example, RGB and CMYK color coordinate systems, hexadecimal representations, and/or the like.

Although certain example embodiments have been described as including glass substrates, it will be appreciated that other types of transparent substrates may be used in different example embodiments. In addition, although certain embodiments have been described in connection with insulating glass units, it will be appreciated that the techniques disclosed herein may be used in connection with monolithic, laminated, vacuum insulating glass (VIG), triple IG units (e.g., units including first, second, and third substrates that are in substantially parallel spaced apart relation to one another), and/or other types of units and/or arrangements.

Furthermore, although certain example embodiments have been described with coatings provided on only one surface, it will be appreciated that a coating may be applied to multiple surfaces. In this regard, although certain example embodiments have been described in connection with a coating on either surface 2 or surface 3, coatings may be provided on both surfaces 2 and 3, on outer surfaces (e.g., for anticondensation or other products), on any one or more of surfaces 1-6 for a triple IG unit, etc. The same or different coatings may be formed on different surfaces in a given arrangement. The same or similar training techniques as described herein may be used to build a database, and the same or similar techniques for comparing color coordinate characterizations and/or characterization changes may be used in such circumstances. It will be appreciated that the presence of multiple coatings may result in reflections associated with uncoated surfaces having a coloration, and that this may be accounted for in the database. In certain example embodiments, an assumption may be made that the first surface will be uncoated, which has been found to significantly help improve the accuracy of coating recognition (e.g., because the reference color of the clear float glass surface can be more accurately determined). In certain example embodiments, this assumption may be set as a user-configurable option.

The terms "heat treatment" and "heat treating" as used herein mean heating the article to a temperature sufficient to achieve thermal tempering and/or heat strengthening of the glass-inclusive article. This definition includes, for example, heating a coated article in an oven or furnace at a temperature of at least about 550 degrees C., more preferably at least about 580 degrees C., more preferably at least about 600 degrees C., more preferably at least about 620 degrees C., and most preferably at least about 650 degrees C. for a sufficient period to allow tempering and/or heat strengthening. This may be for at least about two minutes, up to about 10 minutes, up to 15 minutes, etc., in certain example embodiments.

As used herein, the terms "on," "supported by," and the like should not be interpreted to mean that two elements are directly adjacent to one another unless explicitly stated. In other words, a first layer may be said to be "on" or "supported by" a second layer, even if there are one or more layers therebetween.

Certain example embodiments relate to an electronic coating detection and recognition system comprising a camera. Processing resources include at least one processor and a memory coupled thereto, with the memory tangibly storing instructions that, when performed by the processing resources, at least: capture, using the camera, an image and/or video of an article onto which a source light is shown, the captured image and/or video including source light reflections associated with each major surface of the article; identify a region for each of the source light reflections; calculate a color coordinate characterization for each of the identified source light reflections; detect and recognize any coatings formed on the major surfaces of the article by comparing (a) the calculated color coordinate characterizations and/or changes between calculated color coordinate characterizations to (b) information stored in a database that is backed by a computer readable storage medium and that includes records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed and an identifier of each said detected and recognized coating.

In addition to the features of the previous paragraph, in certain example embodiments, the output may further include a likelihood associated with the detection and recognition of each said detected and recognized coating.

In addition to the features of either of the two previous paragraphs, in certain example embodiments, the output may further include an indication of any likely uncoated surfaces.

In addition to the features of any of the three previous paragraphs, in certain example embodiments, a display device may be provided, e.g., with the output being provided to the display device, e.g., in connection with a user interface presented thereon.

In addition to the features of the previous paragraph, in certain example embodiments, the user interface may be configured to display the captured image and/or video, annotations corresponding to each of the source light reflections, information corresponding to the identifier of each of the detected and recognized coatings, and/or an indication of the location(s) for each of the detected and recognized coatings.

In addition to the features of any of the five previous paragraphs, in certain example embodiments, the source light may be a flame, an LED light source, and/or the like.

In addition to the features of any of the six previous paragraphs, in certain example embodiments, the different known coatings may be different sputter-deposited low-E coatings.

In addition to the features of any of the seven previous paragraphs, in certain example embodiments, the instructions may be further configured to at least: cause ambient lighting conditions to be detected; determine whether the detected ambient lighting conditions are desirable based on pre-stored rules; and optionally, responsive to a determination that the detected ambient lighting conditions are not desirable, issue a human-understandable instruction to a user of the system to adjust the ambient lighting conditions.

In addition to the features of any of the eight previous paragraphs, in certain example embodiments, the instructions may be further configured to at least: detect an angle of the camera relative to the major surfaces of the article; determine whether the angle is within a predetermined range; and optionally (a) responsive to a determination that the angle is within the predetermined range, inform the user that the image and/or video is ready to be taken, and/or (b) responsive to a determination that the angle is not within the predetermined range, issue a human-understandable instruction that an adjustment in the angle needs to be made. Alternatively, or in addition, in addition to the features of any of the eight previous paragraphs, in certain example embodiments, the instructions may be further configured to at least: detect an angle of the camera relative to the major surfaces of the article; determine whether the angle is within a predetermined range; and optionally responsive to a determination that the angle is within the predetermined range, automatically capture the image and/or video.

Certain example embodiments relate to an electronic coating detection and recognition system comprising a camera. Processing resources include at least one processor and a memory coupled thereto, with the memory tangibly storing instructions that, when performed by the processing resources, at least: capture, using the camera, an image and/or video of an article onto which a source light is shown, the captured image and/or video including source light reflections associated with each major surface of the article; and transmit, over a network connection, the captured image and/or video to a remote computer system. The transmission causes the remote computer system to: receive the captured image and/or video; calculate a color coordinate characterization for each of the source light reflections in the received captured image and/or video; detect and recognize any coatings formed on the major surfaces of the article by comparing (a) the calculated color coordinate characterizations and/or changes between calculated color coordinate characterizations to (b) information stored in a data store of the remote computer system that includes records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed and an identifier of each said detected and recognized coating.

In addition to the features of the previous paragraph, in certain example embodiments, the output may further include a likelihood associated with the detection and recognition of each said detected and recognized coating, and/or an indication of any likely uncoated surfaces, e.g., as determined via the remote computer system.

In addition to the features of either of the two previous paragraphs, in certain example embodiments, a display device may be provided, and the instructions may be further configured to receive the output and cause the output to be provided to the display device in connection with a user interface presented thereon.

Certain example embodiments relate to an electronic coating detection and recognition system comprising a camera. Processing resources include at least one processor and a memory coupled thereto, with the memory tangibly storing instructions that, when performed by the processing resources, at least: receive a captured image and/or video of an article onto which a source light is shown, the captured image and/or video including source light reflections associated with each major surface of the article; calculate a color coordinate characterization for each of the source light reflections in the received captured image and/or video; enable detection and recognition of any coatings formed on the major surfaces of the article by comparing (a) the calculated color coordinate characterizations and/or changes between calculated color coordinate characterizations to (b) information stored in a data store, the data store including records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed, an identifier of each said detected and recognized coating, a likelihood associated with the detection and recognition of each said detected and recognized coating, and an indication of any likely uncoated surfaces.

In addition to the features of the previous paragraph, in certain example embodiments, a network interface may be provided, and the captured image and/or video may be received over the network interface and/or the instructions may be further configured to cause the output to be electronically transmitted to a user device via the network interface.

In addition to the features of either of the two previous paragraphs, in certain example embodiments, a camera may be provided and configured to capture the image and/or video.

In addition to the features of any of the three previous paragraphs, in certain example embodiments, an LED light source may be provided and configured to emanate the source light.

In addition to the features of any of the four previous paragraphs, in certain example embodiments, the data store may be a database stored to the memory.

In addition to the features of any of the five previous paragraphs, in certain example embodiments, at least one accelerometer and/or gyroscope may be provided, and the instructions may be further configured to at least gather output from the at least one accelerometer and/or gyroscope and compute a tilt or attitude of smart device, e.g., if the system is or comprises a smartphone.

In addition to the features of any of the 18 previous paragraphs, in certain example embodiments, system may be or may comprise an electronic device such as, for example, smartphone, tablet, or the like, e.g., with the instructions being provided in connection with an application configured to run on the electronic device.

Methods corresponding to any of the 19 previous paragraphs also are contemplated for use in connection with certain example embodiments. For example, in certain example embodiments, there is provided a method for detecting and recognizing coatings, with the method comprising: receiving a captured image and/or video of an article onto which a source light is shown, the captured image and/or video including source light reflections associated with each major surface of the article; calculating a color coordinate characterization for each of the source light reflections in the received captured image and/or video; enabling, via at least one hardware processor, detection and recognition of any coatings formed on the major surfaces of the article by comparing (a) the calculated color coordinate characterizations and/or changes between calculated color coordinate characterizations to (b) information stored in a data store, the data store including records of known color coordinate characterizations and/or known changes between color coordinate characterizations for each of a plurality of different known coatings; and responsive to the detection and recognition of one or more coatings, causing output to be generated, the output indicating the major surface(s) on which each said detected and recognized coating is formed, an identifier of each said detected and recognized coating, a likelihood associated with the detection and recognition of each said detected and recognized coating, and an indication of any likely uncoated surfaces. Similarly, also contemplated for use in certain example embodiments are non-transitory computer readable storage mediums tangibly storing instructions that, when executed by a hardware processor, perform such methods.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electronic coating detection and recognition system for detecting and recognizing a coating on a substrate, the coating detection and recognition system comprising:
   a camera; and
   processing resources including at least one processor and a memory coupled thereto, the memory tangibly storing instructions that, when performed by the processing resources, are configured to at least:
   capture, using the camera, an image and/or video of an article onto which a source light is shown, the captured image and/or video including source light reflections associated with each major surface of the article;
   identify a region for each of the source light reflections;
   calculate a color coordinate characterization for each of the identified source light reflections;
   detect and recognize any coatings formed on the major surfaces of the article by comparing (a) the calculated color coordinate characterizations and/or changes between calculated color coordinate characterizations to (b) information stored in a database that is backed by a computer readable storage medium and that includes records of known color coordinate characterizations and/or known changes between color coordinate characterizations for each of a plurality of different known coatings; and
   responsive to the detection and recognition of one or more coatings, cause output to be generated, the output indicating the major surface(s) on which each said detected and recognized coating is formed and an identifier of each said detected and recognized coating.

2. The system of claim 1, wherein the output further includes a likelihood associated with the detection and recognition of each said detected and recognized coating.

3. The system of claim 2, wherein the output further includes an indication of any likely uncoated surfaces.

4. The system of claim 1, further comprising a display device, the output being provided to the display device in connection with a user interface presented thereon.

5. The system of claim 4, wherein the user interface is configured to display the captured image and/or video, annotations corresponding to each of the source light reflections, information corresponding to the identifier of each of the detected and recognized coatings, and an indication of the location(s) for each of the detected and recognized coatings.

6. The system of claim 1, wherein the source light is a flame.

7. A smartphone including the system of claim 1, the instructions being provided in connection with an application configured to run on the electronic smartphone.

8. The smartphone of claim 7, further comprising an LED light source configured to provide the source light.

9. The system of claim 1, wherein the different known coatings are different sputter-deposited low-E coatings.

10. The system of claim 1, wherein the instructions are further configured to at least:
    cause ambient lighting conditions to be detected;
    determine whether the detected ambient lighting conditions are desirable based on pre-stored rules; and
    responsive to a determination that the detected ambient lighting conditions are not desirable, issue a human-understandable instruction to a user of the system to adjust the ambient lighting conditions.

11. The system of claim 1, wherein the instructions are further configured to at least:
    detect an angle of the camera relative to the major surfaces of the article;
    determine whether the angle is within a predetermined range; and
    (a) responsive to a determination that the angle is within the predetermined range, inform the user that the image and/or video is ready to be taken, and/or (b) responsive to a determination that the angle is not within the predetermined range, issue a human-understandable instruction that an adjustment in the angle needs to be made.

12. The system of claim 1, wherein the instructions are further configured to at least:
    detect an angle of the camera relative to the major surfaces of the article;
    determine whether the angle is within a predetermined range; and
    responsive to a determination that the angle is within the predetermined range, automatically capture the image and/or video.

13. An electronic coating detection and recognition system, comprising:
    a camera; and
    processing resources including at least one processor and a memory coupled thereto, the memory tangibly storing instructions that, when performed by the processing resources, at least:
    capture, using the camera, an image and/or video of an article onto which a source light is shown, the captured image and/or video including source light reflections associated with each major surface of the article; and
    transmit, over a network connection, the captured image and/or video to a remote computer system, the transmission causing the remote computer system to:
    receive the captured image and/or video;
    calculate a color coordinate characterization for each of the source light reflections in the received captured image and/or video;
    detect and recognize any coatings formed on the major surfaces of the article by comparing (a) the calculated color coordinate characterizations and/or changes between calculated color coordinate characterizations to (b) information stored in a data store of the remote computer system that includes records of known color coordinate characterizations and/or known changes between color coordinate characterizations for each of a plurality of different known coatings; and responsive to the detection and recognition of one or more coatings, cause output to be generated, the output indicating the major surface(s) on which each said detected and recognized coating is formed and an identifier of each said detected and recognized coating.

14. The system of claim 13, wherein the output further includes a likelihood associated with the detection and recognition of each said detected and recognized coating, as well as an indication of any likely uncoated surfaces, as determined via the remote computer system.

15. The system of claim 13, further comprising a display device, wherein the instructions are further configured to receive the output and cause the output to be provided to the display device in connection with a user interface presented thereon.

16. An electronic coating detection and recognition system, comprising:
processing resources including at least one processor and a memory coupled thereto, the memory tangibly storing instructions that, when performed by the processing resources, at least:
receive a captured image and/or video of an article onto which a source light is shown, the captured image and/or video including source light reflections associated with each major surface of the article;
calculate a color coordinate characterization for each of the source light reflections in the received captured image and/or video;
enable detection and recognition of any coatings formed on the major surfaces of the article by comparing (a) the calculated color coordinate characterizations and/or changes between calculated color coordinate characterizations to (b) information stored in a data store, the data store including records of known color coordinate characterizations and/or known changes between color coordinate characterizations for each of a plurality of different known coatings; and
responsive to the detection and recognition of one or more coatings, cause output to be generated, the output indicating the major surface(s) on which each said detected and recognized coating is formed, an identifier of each said detected and recognized coating, a likelihood associated with the detection and recognition of each said detected and recognized coating, and an indication of any likely uncoated surfaces.

17. The system of claim 16, further comprising a network interface, wherein the captured image and/or video is received over the network interface.

18. The system of claim 17, wherein the instructions are further configured to cause the output to be electronically transmitted to a user device via the network interface.

19. The system of claim 16, further comprising a camera configured to capture the image and/or video.

20. The system of claim 19, further comprising an LED light source configured to illuminate the source light.

21. The system of claim 20, wherein the data store is a database stored to the memory.

22. The system of claim 16, being a smart device.

23. The system of claim 22, further comprising at least one accelerometer and/or gyroscope, wherein the instructions are further configured to at least gather output from the at least one accelerometer and/or gyroscope and compute a tilt or attitude of smart device.

24. A method for detecting and recognizing coatings, the method comprising:
receiving a captured image and/or video of an article onto which a source light is shown, the captured image and/or video including source light reflections associated with each major surface of the article;
calculating a color coordinate characterization for each of the source light reflections in the received captured image and/or video;
enabling, via at least one hardware processor, detection and recognition of any coatings formed on the major surfaces of the article by comparing (a) the calculated color coordinate characterizations and/or changes between calculated color coordinate characterizations to (b) information stored in a data store, the data store including records of known color coordinate characterizations and/or known changes between color coordinate characterizations for each of a plurality of different known coatings; and
responsive to the detection and recognition of one or more coatings, causing output to be generated, the output indicating the major surface(s) on which each said detected and recognized coating is formed, an identifier of each said detected and recognized coating, a likelihood associated with the detection and recognition of each said detected and recognized coating, and an indication of any likely uncoated surfaces.

25. A non-transitory computer readable storage medium tangibly storing instructions that, when executed by a hardware processor, perform the method of claim 24.

* * * * *